United States Patent
Magowan et al.

[11] Patent Number: 5,945,830
[45] Date of Patent: Aug. 31, 1999

[54] FLOW THROUGH FLUID PH AND CONDUCTIVITY SENSOR

[75] Inventors: Arthur Magowan, Stow; Ernest J. Woods, III, Upton, both of Mass.

[73] Assignee: Biosepra, Inc., Marlborough, Mass.

[21] Appl. No.: 08/840,805

[22] Filed: Apr. 16, 1997

Related U.S. Application Data

[60] Provisional application No. 60/016,328, Apr. 26, 1996.

[51] Int. Cl.$^6$ .................................................. G01N 27/28
[52] U.S. Cl. ........................ 324/438; 324/439; 324/450; 204/433; 205/787.5; 436/163
[58] Field of Search ..................... 324/438, 439, 324/450; 204/433; 205/787.5; 422/82.02; 436/163

[56] References Cited

U.S. PATENT DOCUMENTS

| | | | |
|---|---|---|---|
| 3,584,964 | 6/1971 | Nejame, Jr. ............................. | 356/244 |
| 3,648,159 | 3/1972 | Stansell et al. ........................ | 324/438 |
| 3,648,160 | 3/1972 | Beaver .................................. | 324/442 |
| 3,762,214 | 10/1973 | Bogusz ................................. | 73/61 R |
| 3,936,729 | 2/1976 | Winslow, Jr. ........................... | 324/450 |
| 4,196,383 | 4/1980 | Teass, Jr. .............................. | 324/438 |
| 4,283,262 | 8/1981 | Cormier et al. .................... | 204/195 M |
| 4,359,638 | 11/1982 | Allport ................................... | 378/50 |
| 4,447,775 | 5/1984 | Breuker et al. ........................ | 324/438 |
| 4,504,790 | 3/1985 | Frant ...................................... | 324/439 |
| 4,590,424 | 5/1986 | Girot et al. ............................. | 324/204 |
| 4,609,874 | 9/1986 | Reich .................................... | 324/438 |
| 4,803,869 | 2/1989 | Barcelona et al. ................. | 324/438 X |
| 5,008,627 | 4/1991 | Tsutsuta et al. ....................... | 324/444 |
| 5,037,737 | 8/1991 | Liffmann et al. ........................ | 435/11 |
| 5,103,179 | 4/1992 | Thomas et al. ........................ | 324/438 |
| 5,138,264 | 8/1992 | Seki et al. ............................. | 324/439 |
| 5,194,814 | 3/1993 | D'Couto ................................. | 324/446 |
| 5,268,092 | 12/1993 | Eden .................................. | 324/438 X |
| 5,332,494 | 7/1994 | Eden et al. ......................... | 324/438 X |
| 5,342,510 | 8/1994 | Eden et al. ......................... | 324/438 X |
| 5,399,256 | 3/1995 | Bohs et al. ............................ | 204/409 |

*Primary Examiner*—Glenn W. Brown
*Attorney, Agent, or Firm*—Heslin & Rothenberg, P.C.

[57] ABSTRACT

A sensor for measuring pH and conductivity for liquids is disclosed. The sensor includes a housing having a pH cell and a conductivity cell. A pH fluid flow path is defined between a pH cell fluid inlet and pH cell fluid outlet. An aperture within the pH cell is adapted to receive an electronic pH probe therein. The aperture is configured to position an end of the pH probe having a pH sensing area therein and juxtaposition to the pH fluid flow path so that fluid flowing within the flow path is exposed to the pH sensing area of the electronic pH sensor. A conductivity cell is adapted for placement of a conductivity sensor therein. The conductivity sensor is disposed between a conductivity cell fluid inlet and conductivity cell fluid outlet so that fluid flowing therethrough contacts the conductivity sensor.

59 Claims, 7 Drawing Sheets

FLOW THROUGH FLUID PH AND CONDUCTIVITY SENSOR

CLAIM OF PRIORITY

This application claims the priority of United States Provisional patent application Ser. No. 60/016,628 filed on Apr. 26, 1996.

FIELD OF THE INVENTION

The present invention relates to a sensor of pH and conductivity in a fluid, and more particularly, to a sensor for pH and conductivity which allows a liquid under pressure to flow through one or more cells which measure pH and conductivity of the liquid.

BACKGROUND OF THE INVENTION

Generally, the sampling of liquids to determine its pH and conductivity (or ionic concentration) is accomplished using batch processing. A sample of the liquid to be tested is placed within a container and probes, sensors, or other measuring devices inserted therein to detect the pH and conductivity of the fluid. However, measuring both the pH and conductivity of a fluid using this type of batch processing may be time consuming and may yield time delayed results. Therefore, when it is necessary to test fluids flowing through a system, batch processing may provide pH and conductivity results which do not accurately reflect the current pH and/or conductivity of the fluid within the system.

It is therefore desirable to achieve a dual functioning pH and conductivity sensor for liquids which allows liquids which are the subject of a processing system or the like to flow therethrough thereby measuring pH and conductivity on a continual, real-time basis.

It is also desirable to achieve such a dual functioning pH and conductivity sensor which allows for optimal sensing of the fluid.

SUMMARY OF THE INVENTION

The aforementioned advantages may be achieved by using the dual functioning pH and conductivity sensor for liquids constructed in accordance with the principles of the present invention.

The sensor includes a housing having a pH cell and/or conductivity cell therein. A fluid inlet and outlet are disposed within the pH cell and define a pH fluid flow path therebetween. An aperture is located within the pH cell and is adapted to receive an electronic pH probe therein. The aperture is configured to position an end of the electronic pH probe having a pH sensing area therein in juxtaposition to the pH fluid flow path so that fluid flowing within the fluid flow path is exposed to the pH sensing area of the pH sensor. The sensor may also include a conductivity cell adapted for placement of the conductivity sensor therein. The conductivity sensor may be disposed between a fluid inlet and outlet of the conductivity cell so that fluid flowing from the fluid inlet through the conductivity cell and out the fluid outlet contacts the conductivity sensor. The pH cell fluid outlet may be in fluid flow relationship to the conductivity cell fluid inlet so that fluid flowing from the pH cell fluid outlet will then flow into the conductivity cell fluid inlet.

A means for retaining the pH probe within the pH cell may include a threaded area on the housing adapted to receive a retaining nut therein. The retaining nut may have an aperture for receiving the electronic pH probe therethrough. An O-ring may be disposed on a lip of the pH probe and contact a ridge within the pH fluid cell to form a liquid tight seal when the pH probe is inserted into the aperture of the pH cell.

The fluid flow path may be defined by the end of the electronic pH probe having a pH sensing area inserted into the receptacle and by an end wall of the pH cell. A first portion of the pH fluid flow path starting from the pH cell fluid inlet and ending a point juxtaposed to the pH sensing area of the pH sensing probe progressively expands in width. A second portion of the flow path starting from a point juxtaposed to the pH sensing area and ending at said pH cell fluid outlet progressive decreases in width. A portion of the end wall defining the flow path may be oriented at an angle, preferably of 12°. A second portion of the end wall defining the flow path may be oriented at a second angle, preferably a −12°.

The conductivity sensor may include a positive electrode and a negative electrode, the electrodes being separated by a gap therebetween. The conductivity sensor may be disposed to allow a liquid from within the conductivity cell to flow through the conductivity cell fluid inlet and into the gap between the electrodes. Each of the electrodes may comprise a cylinder having an aperture extending therethrough. The aperture may be disposed to allow liquid flowing within the conductivity cell to flow therethrough and into the gap, and the electrodes may be disposed so that the apertures of each electrode are coaxially aligned. Also, the apertures may be coaxially aligned with the conductivity cell fluid inlet and conductivity cell fluid outlet so that fluid flows in a stream along an axis through the conductivity sensors and gap therebetween.

A means for supporting the electrodes within the conductivity cell may also be included. The means may comprise a molded part having a first receptacle in juxtaposition to a second receptacle. The receptacles may be oriented to maintain the axial alignment between the apertures of the electrodes and to maintain the gap between the electrodes. The apertures may extend through the center of the cylindrically shaped electrodes, and the molded part may contain an aperture between the receptacles at an area defined by said gap to allow fluid to flow therethrough.

The conductivity sensor may also include a means for sealing the conductivity sensor in the conductivity cell. The sealing means may include a pair of O-rings; each of the pair being disposed about the electrodes to prevent fluid from flowing outside of the apertures. The O-rings may contact the top surface of the conductivity cell and a bottom surface of the conductivity cell, respectively. Each electrode may also include a means for connecting an electrical conductor thereto. The means may be a hollow post, brazed to a cylindrical portion of the electrode. A cap may be adapted to cover an opening in the housing leading to the conductivity cell; the conductivity cell may be filled with a potting material.

The invention may also include a method of measuring pH and/or conductivity. The method includes flowing the fluid into a pH cell fluid inlet, widening the stream of fluid and making it more shallow as it passes a pH sensing area of the electronic pH probe so that the stream covers the sensing area, and sensing the pH of the fluid within the stream covering the sensing area.

The method may also include flowing the fluid into a conductivity cell wherein the conductivity of the fluid is measured. The fluid may be flowed in a stream into a gap located between the electrodes of a conductivity sensor within the conductivity cell.

BRIEF DESCRIPTION OF THE DRAWINGS

The invention may readily be understood by reading the detailed description together with the corresponding drawings in which.

DETAILED DESCRIPTION OF THE DRAWINGS

Figure 1:
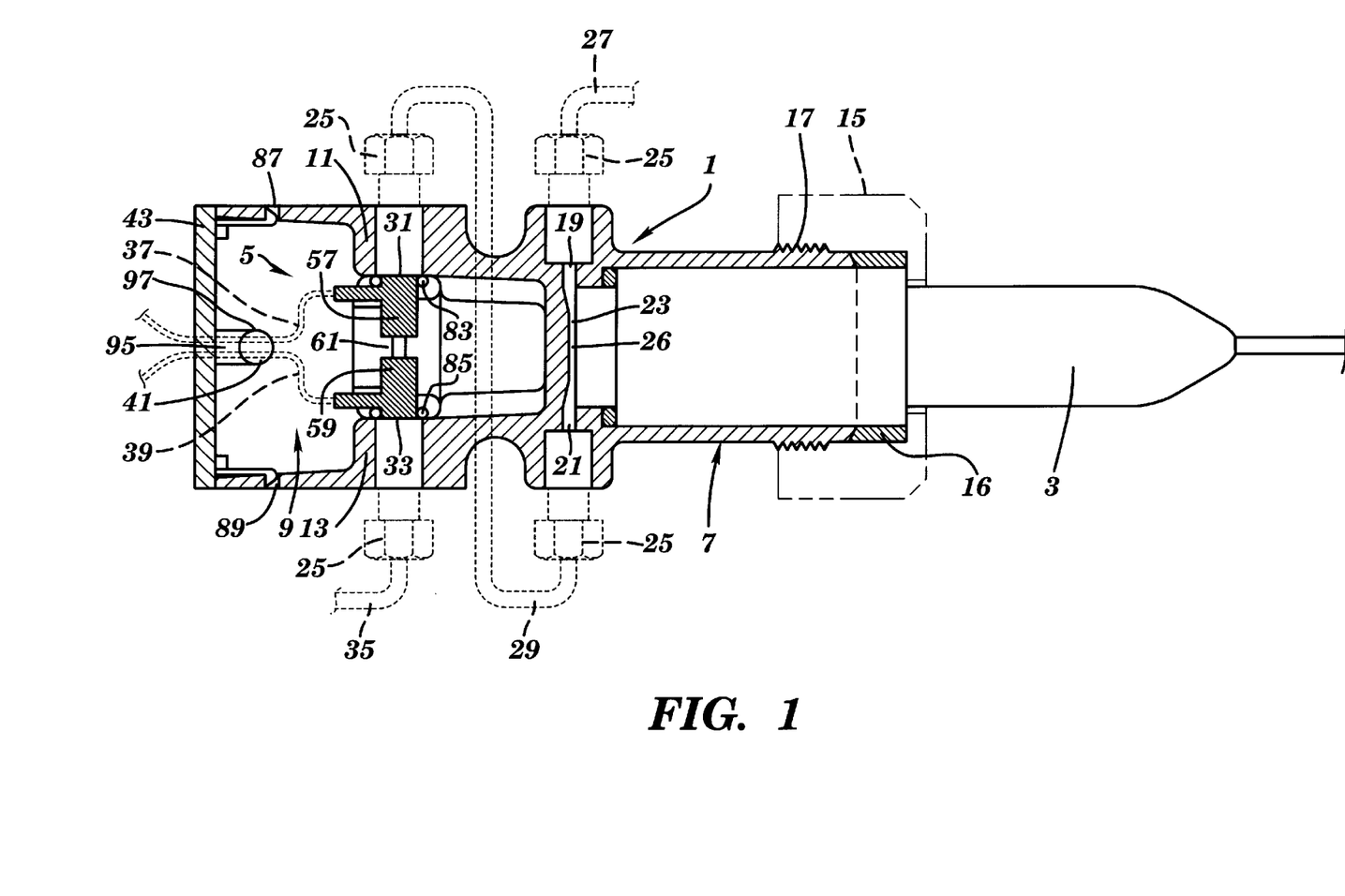
FIG. 1 depicts a sectional view from the side of a pH and conductivity sensor for liquids constructed in accordance with the principles of the present invention.

Referring to FIG. 1, a combination pH and conductivity sensor for liquids is shown. The sensor includes a housing 1, an electronic pH probe 3, and a conductivity sensor 5. The housing 1 is divided into two cells, a pH cell 7 wherein the pH probe 3 is inserted, and a conductivity cell 9 wherein the conductivity sensor 5 is inserted.

Figure 5A:
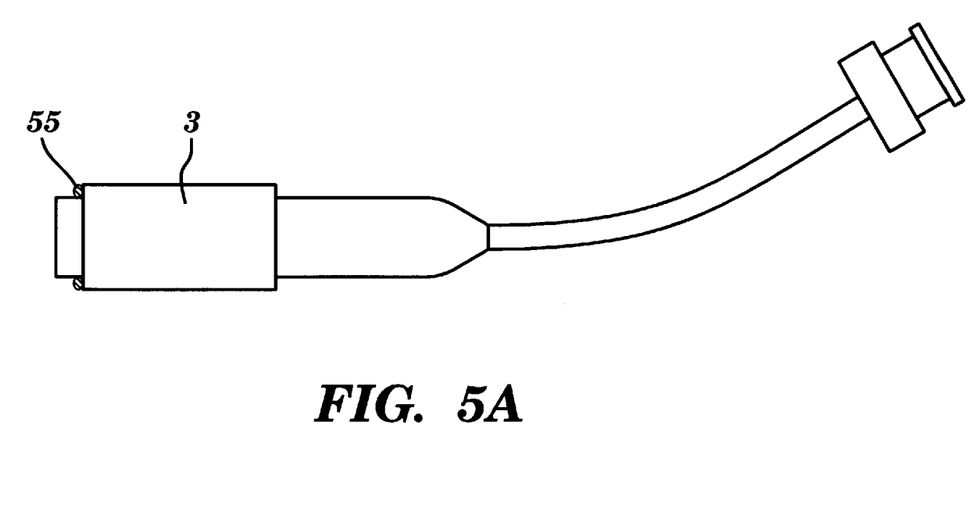
FIG. 5A depicts a pH probe insertable within the housing as shown in FIGS. 2A, 2D, 2E, 3A and 3B.
Figure 5B:
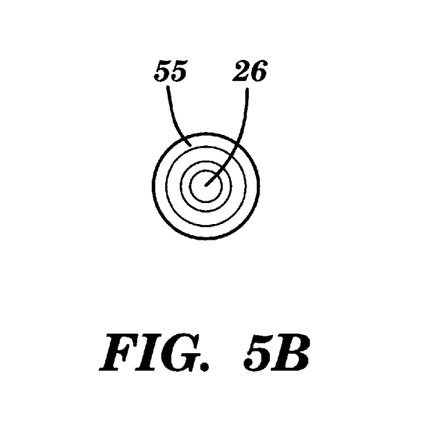
FIG. 5B depicts an end view of the pH probe depicted in FIG. 5A.

In the embodiment shown in FIG. 1, the pH cell 7 is separated from, and faces opposite to, the conductivity cell 9. The conductivity sensor 5 is maintained within the conductivity cell 9 between a pair of ribs 11, 13. A pH cell fluid inlet 19 and a fluid outlet 21 allow fluid to flow into and out of the pH cell, respectively. Located between the fluid inlet 19 and fluid outlet 21 is a fluid flow path 23 within the pH cell 7. A compression fitting 25 is affixed to the housing 1 to allow fluid from an inlet tube 27 to flow into the pH cell fluid inlet 19 through the fluid flow path 23 and out of the fluid outlet 21 of the pH cell 7. As fluid flows through the flow area 23 it flows in front of a sensing area 26 of the electronic pH sensor 3 where the pH of the fluid is sensed. The sensing area 26 of the pH sensor as depicted in FIG. 5B is preferably covered with glass to accurately read the pH of the fluid flowing thereby when the pH sensor 3 is mounted into the pH cell 7 as is shown in FIG. 1. An O-ring 55 as depicted in FIGS. 1, 5A and 5B is mounted about a lip of the pH sensor 3 to effectively seal the pH cell 7 and prevent fluid from leaking thereout.

A conductivity cell fluid inlet 31 and a fluid outlet 33 allow fluid to flow into the conductivity cell and out of the conductivity cell 9, respectively. A compression fitting 25 is located on or placed onto the housing to allow fluid to flow into the fluid inlet 31. An intermediate tube 29 places the pH cell fluid outlet 21 in fluid flow relationship to the conductivity cell fluid inlet 31 using compression fittings so that fluid will flow from the pH cell to the conductivity cell. Fluid flowing into the inlet 31 of the conductivity cell will then flow past the conductivity sensor 5 where its conductivity will be sensed and then out of the conductivity cell fluid outlet 33 through an outlet tube 35 affixed thereto by another compression fitting. The conductivity sensor 5 is sized to fit tightly between the ribs 11, 13 within the conductivity cell. A pair of electrical conductors 37, 39 lead from the conductivity sensor out of the conductivity cell 9 through an aperture 41. The aperture is formed between an end cap 43 and a portion of the housing 1 defining the conductivity cell 9.

The sensor housing is capable of receiving fluid under pressure from the inlet tube 27 leading to the pH cell where the pH sensor 3 will sense the pH of the fluid. Thereafter, fluid will flow via the intermediate tube 29 into the conductivity cell 9 where the conductivity of the fluid will be sensed by the conductivity sensor 5 before exiting the sensor through the outlet tube 35. The pH sensor 3 is affixed to the housing 1 by a retaining nut 15 which is threadably engaged to a threaded section 17 at the opening of the pH cell. The retaining nut has an aperture therethrough within which the pH sensor is inserted. A ring 16, through which the pH sensor is also inserted, is located between the threaded section and the retaining nut 15

Figure 2A:
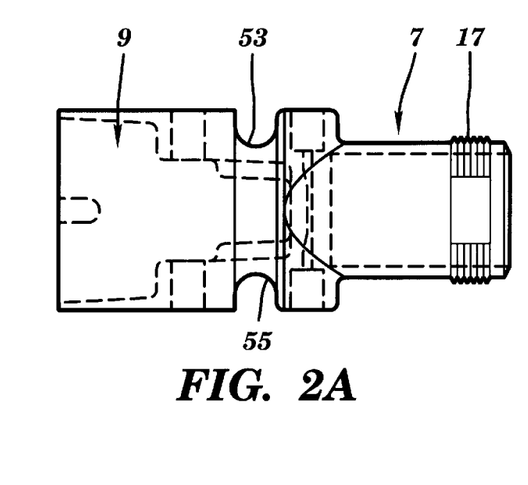
FIG. 2A depicts a side view of the housing of the sensor depicted in FIG. 1 and constructed in accordance with the principles of the present invention.
Figure 2B:
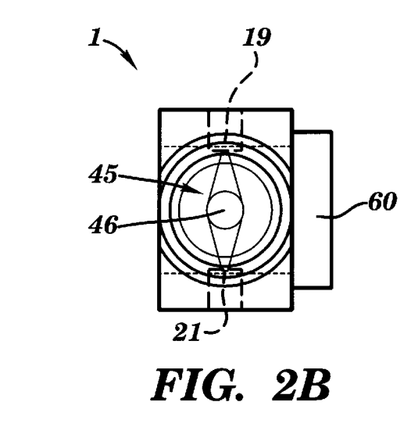
FIG. 2B depicts a front view of the housing depicted in FIG. 2A.
Figure 2C:
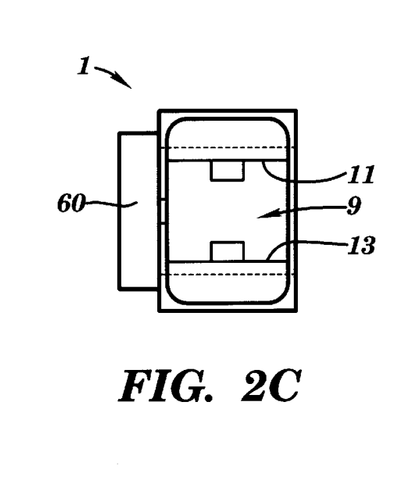
FIG. 2C depicts an end view of the housing depicted in FIGS. 2A and 2B.

Referring to FIGS. 2A–2E, the particulars of the housing 1, will now be described. The pH chamber 7 contains an opening or aperture therein which receives the pH probe 3 (as shown in FIG. 1). As shown in FIG. 2A, the cross-sectional area of the pH chamber 7 is configured to receive the body of the pH probe so that there is a snug fit therebetween. Referring to FIG. 2C, the cross-sectional configuration of the conductivity cell 9 is shown. Ribs 11, 13 protrude from the top and bottom thereof, respectively. The conductivity sensor 5 fits between the ribs 11, 13, as shown in FIG. 1, and is held therein by friction therebetween.

Referring to FIG. 2B, the interior of the pH cell is shown. A flow area, generally referred to as 45, extends between the fluid inlet 19 and fluid outlet 21. Both the inlet and outlet are, preferably, of 0.060 inches in diameter. The flow area near the fluid inlet 19 is generally narrower than the flow area near the center point 46 of pH chamber. The flow area is widest at the center point 46 of the pH chamber 7. The center point 46 is aligned and coaxial with the center of the reading area 26 of the pH probe 3 (see FIG. 1). The flow area below the center 46 of the pH cell 7 progressively narrows until it reaches the fluid outlet 21. This flow area 45 configuration effectively allows fluid flowing through the inlet 19, which is preferably of circular cross-section as shown in FIG. 2E, to spread out progressively wider as the fluid falls downward towards the center 46 of the pH cell 7 adjacent to the reading area 25 (FIG. 1). Therefore, fluid flowing through the inlet 19 will progressively widen while becoming shallower until reaching the center point 46 when the fluid will thereafter narrow and become deeper until it reaches the outlet 21.

Figure 2D:
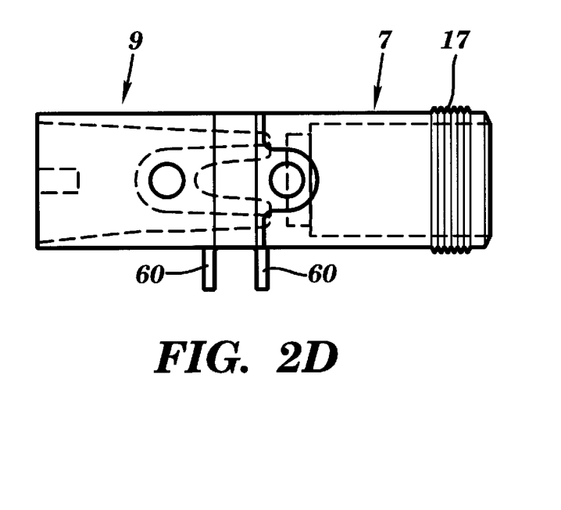
FIG. 2D depicts a top view of the housing depicted in FIGS. 2A, 2B and 2C.
Figure 2E:
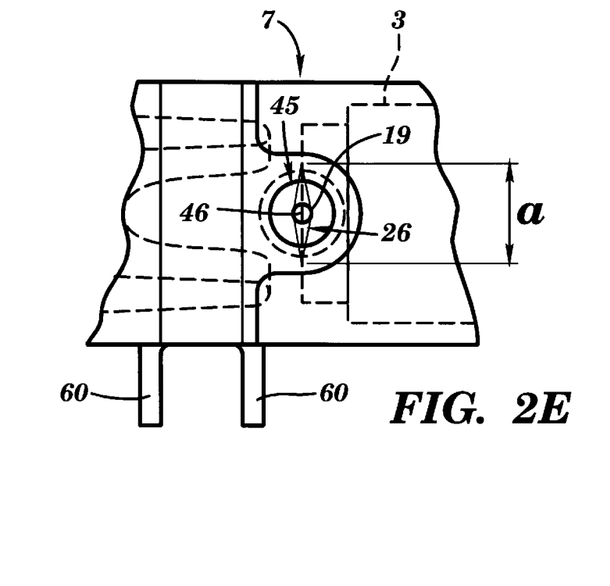
FIG. 2E depicts a top view of the pH cell third inlet within the housing depicted in FIGS. 2A, 2B, 2C and 2D.
Figure 3A:
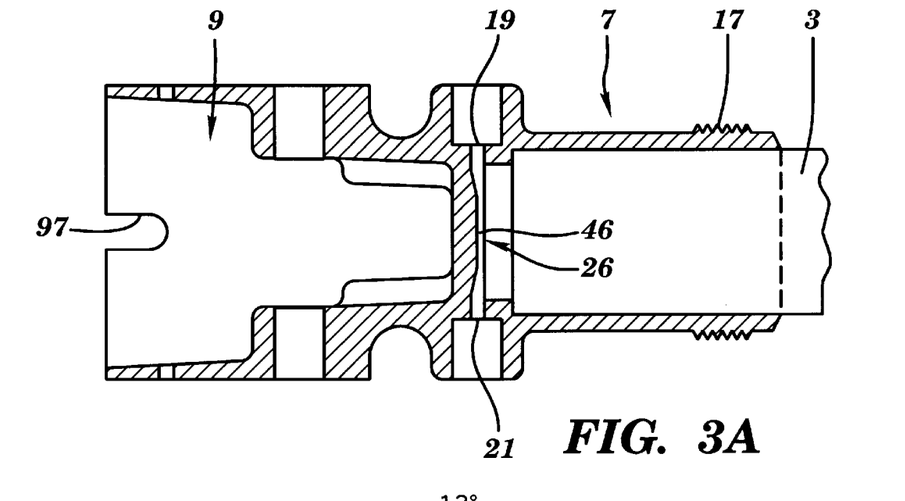
FIG. 3A depicts a sectional view of the housing depicted in FIG. 2D.
Figure 3B:
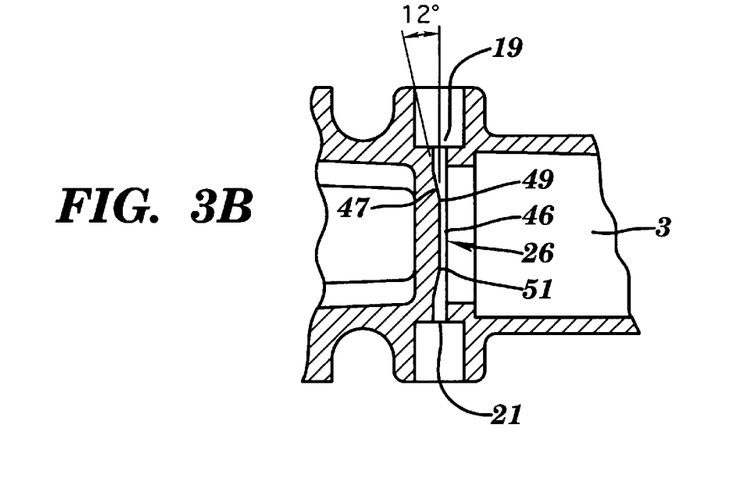
FIG. 3B depicts a sectional view of the pH cell fluid inlet and outlet within the housing depicted in FIG. 3A.

FIG. 2E depicts the width of the flow area 45 at its widest point adjacent to the sensing area of the pH probe 3 within the pH cell 7. The width of the flow area 45 corresponds to the diameter of the sensing area represented by dimension "a", preferably 0.250 inches. Referring to FIGS. 3A and 3B, as the fluid flows past this center point 46, it then enters the lower portion of the flow area 45 where the fluid progressively narrows until it reaches the fluid outlet 21, which is preferably of circular cross-section. Fluid will decrease in velocity as it progresses towards the center of the flow area 45. This occurs because the volume of the flow area 45 progressively increases towards the center thereof. Since at the center portion of the flow area adjacent to the sensing area 26 of the pH sensor 3 (shown in FIG. 1) the fluid stream is widest, it is flowing at its lowest velocity so that the pH sensor 3 may accurately sense the pH of the fluid flowing therebefore. As fluid flows past the sensing area 26, the volume of the flow area 45 progressively decreases therefore progressively increasing the fluid flow rate until the fluid exits the pH cell 7 through the fluid outlet 21. The widest cross-sectional fluid flow area at central point 46 near the sensing area 26 should be less than or equal to between one and two times the cross sectional flow area at the pH cell fluid inlet 19. However, the area at the sensing area should preferably be about one and one half times the area of the inlet.

Referring still to FIGS. 3A and 3B, the flow area 45 contains an angled wall 47 which comprises a portion of a wall defining the pH cell 7. The wall extends at an angle, preferably of twelve degrees, from a point 49 juxtaposed to the top edge of the sensing area 26 the pH probe located between point 49 and point 51. This portion of the wall juxtaposed to the sensing area 26 of the pH probe 3 is not angled and is parallel to the sensing area 26. Preferably, the space between this portion of the wall and the sensing area is, preferably, 0.020 inches. However, the portion of the wall below this opposite point 51 extends in a reverse angle, preferably −12° until it reaches fluid outlet 21. The configuration of the flow area (as depicted in FIGS. 2B, 2E and 3B) increases the ability of the pH sensor 3 to provide optimal pH readings of fluid flowing past the sensing area 25. Accordingly, greater accuracy in pH readings of various fluid may be achieved through such a configuration.

Figure 4:
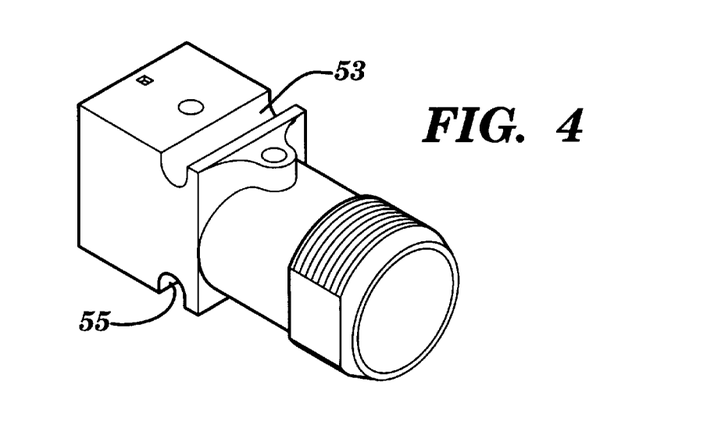
FIG. 4 depicts an isometric view of the housing depicted in FIGS. 1, 2A–2D, 3A and 3B.

Referring to FIGS. 2A and 2D, a means for mounting the sensor 1 is shown. A pair of channels 53, 55 are formed on the top side and bottom side of the sensor, respectively, to allow fasteners to be inserted therein. A pair of flanges 60 as shown in FIG. 2D, protrude from one side of the sensor 1 and are parallel to the channels 53, 55 to effectively increase the length of these channels. However, the flanges 60 may be omitted, as shown in FIG. 4, if desired.

Figure 7A:
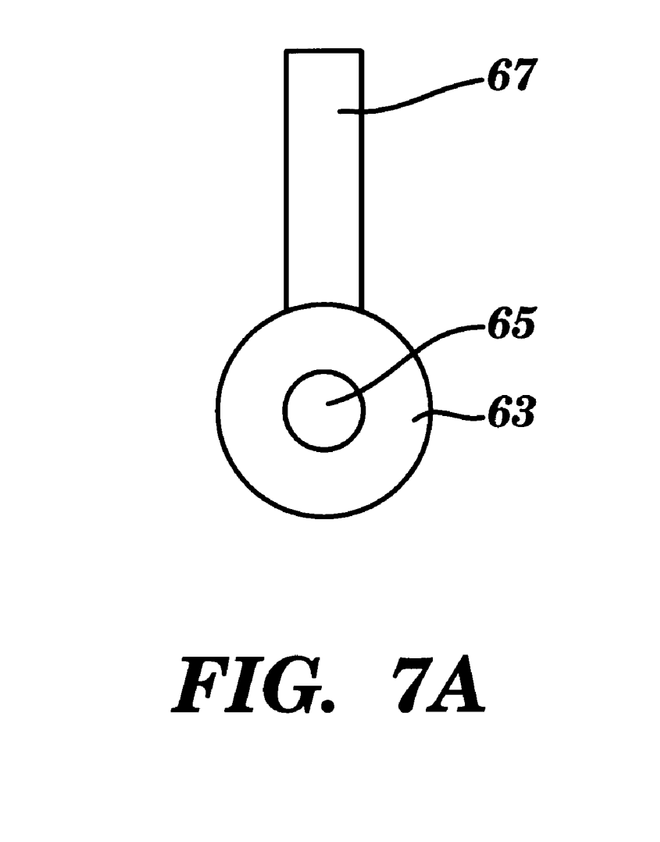
FIG. 7A depicts one electrode of the conductivity sensor insertable within the conductivity cell of the housing as depicted in FIG. 1.
Figure 7B:
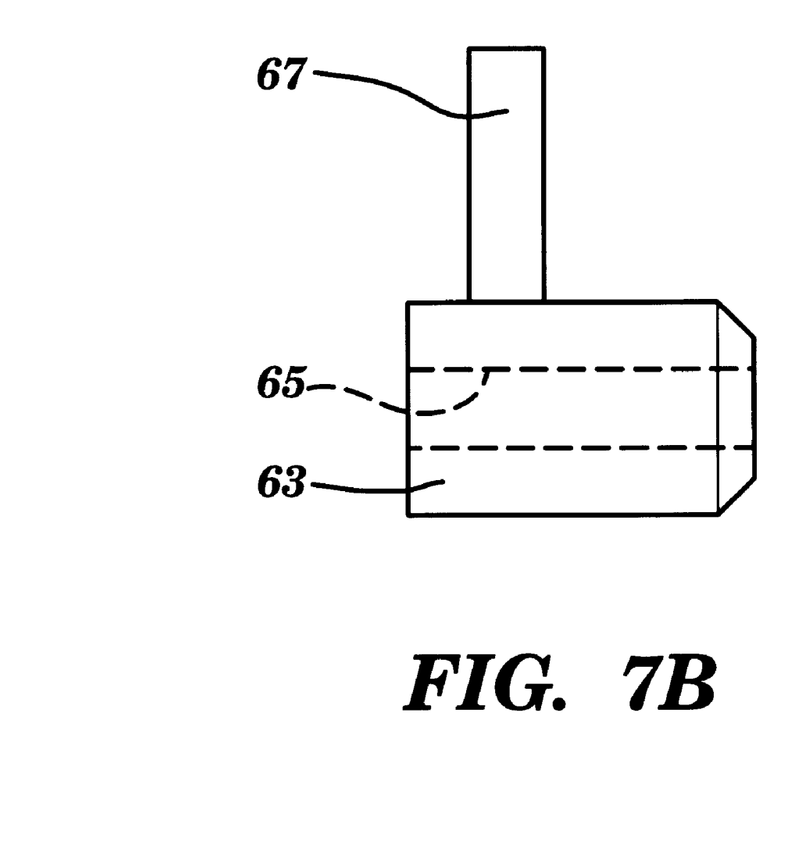
FIG. 7B depicts a side view of the electrode depicted in FIG. 7A.

Referring now to FIG. 1 and FIGS. 7A–8C, the various components of the conductivity sensor 5 will now be described. A pair of electrodes, 57, 59, shown in FIG. 1, are oriented such that a gap 61 is located therebetween. Preferably, the gap should be 0.050 inches and maintained at this distance to provide accurate and precise readings of the conductivity of fluid which flows between this gap. Each electrode is configured as shown in FIGS. 7A and 7B. A cylindrical portion 63 contains an aperture 65 in the center thereof and extending completely therethrough. A post 67 extends, preferably perpendicularly, from the cylindrical portion 63 and is adapted to receive an electrical conductor therein. Preferably, the post is hollow so that an electrical conductor can be inserted therein and preferably soldered. The post is typically silver-brazed to the electrode to provide for sufficient conductivity therebetween.

Figure 8A:
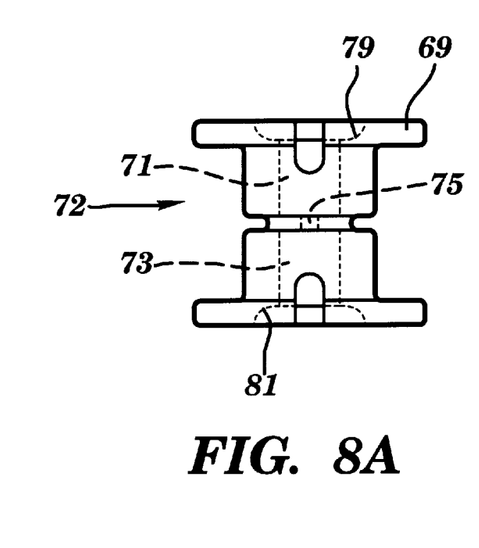
FIG. 8A–8C depict a mold usable for supporting the electrode of FIG. 7A–7B.
Figure 8B:
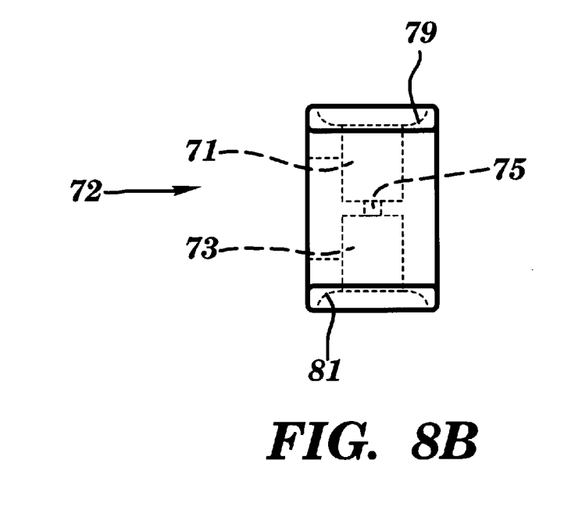
Figure 8C:
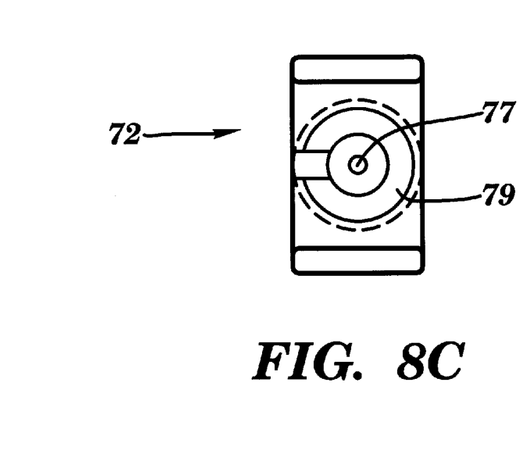

A mold 72 may be used as a means for supporting the electrodes within the conductivity cell. as shown in FIGS. 8A–8C, the mold 72 is configured to receive a pair of identical electrodes having cylindrical shapes therein such that the electrodes are diametrically opposed to one another when placed within the mold as shown in FIG. 1. The mold contains a top receptacle 71 which has a cylindrical section for receiving a first electrode therein and a bottom receptacle 73 which also has a cylindrical section for receiving a second electrode therein. Between the receptacles 71, 73 is an aperture 75 which coaxially aligns with the apertures 65 in each of the electrodes 57, 59 thereby forming a continuous bore 77 through the mold and electrodes therein. Within the top receptacle 71 of the mold exists a lip 79 at a top end thereof. A similar lip 81 is located at the lower end of the mold at the bottom receptacle 73. An O-ring 83 fits in the top receptacle on a lip 79 thereof, as shown in FIG. 1. A second O-ring 85 sits on the lip of the bottom receptacle 73, also as shown in FIG. 1. When the conductivity sensor is fully assembled and inserted into the conductivity cell as shown in FIG. 1, these O-rings create a seal between the mold and the ribs 11, 13, respectively, to prevent fluid flowing within the conductivity cell from leaking therefrom. The O-rings allow fluid to flow into the continuous bore 77 and between the electrode gap where the conductivity thereof can be sensed prior to the fluid flowing through the outlet 33 of the conductivity cell and eventually through the outlet tube 35.

Figure 6A:
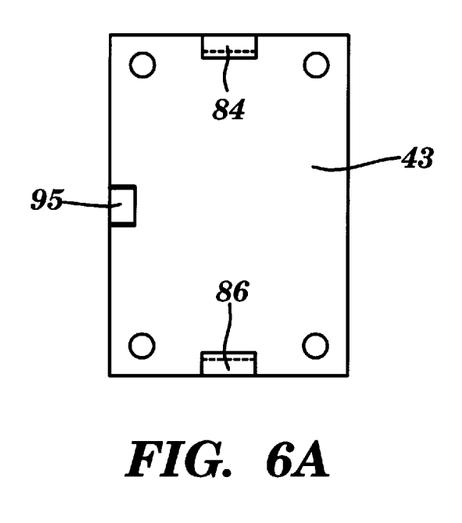
FIG. 6A depicts an end view of an end cap attachable to an opening within the conductivity cell of the housing as depicted in FIG. 1.
Figure 6B:
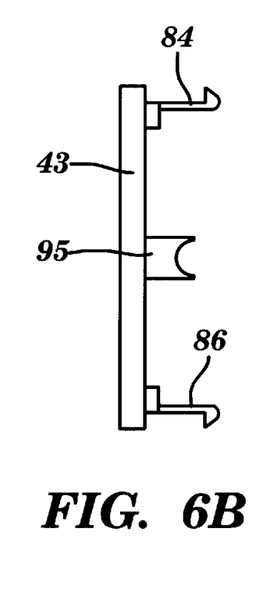
FIG. 6B depicts a side view of the end cap of FIG. 6A.
Figure 6C:
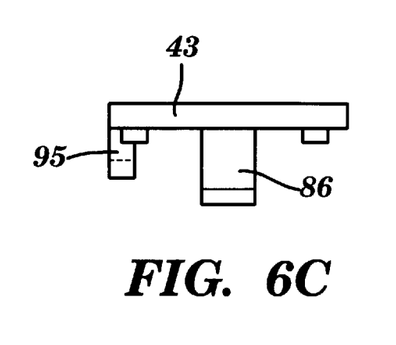
FIG. 6C depicts a side view of the end cap of FIGS. 6A and 6B.

As shown in FIG. 1, an end cap 43 fits into the opening leading into the conductivity cell 9 thereby closing the same. Referring to FIGS. 6A–6C, a pair of wings 84, 86, protruding from the edges of the end cap 43 are sized and oriented to be received by a pair of receiving means such as apertures 87, 89, respectively. The receiving means receives the wings and prevents the cap from being removed from the conductivity cell 9 without manipulation of the wings 84, 86. One or more studs may be located on the inner surface of the end cap to align the end cap within the opening of the conductivity cell 9. Referring to FIG. 1 and 6B, a protrusion 95 extends from one side of the end cap 43 into a window 97 to form an aperture 41. This allows the electrical conductors 37, 41 each of which are preferably insulated and extend from the post of an electrode 57, 59, respectively, to pass through the aperture 41 and connect to an electronic device. A potting material is placed within the conductivity cell to seal the entire contents thereof.

During use, the sensor, may be mounted in any convenient location where fluid can flow therethrough for sensing of the pH and conductivity thereof. Fluid should be flowed through the inlet tube 27 where it will then flow into the pH chamber 7 and flow area 23 therein. As fluid passes the sensing area 25 of the pH probe 3, the pH probe electronically senses the pH of the fluid. The pH probe, available from Sensorex of 11661 Seaboard Circle, Stanton, Calif., 90680, may be connected to a computer or other electronic device for converting the electrical signal therefrom into a pH reading. The pH reading may be continuously monitored so that instantaneous real time readings of the pH flowing through the flow area 23, corresponding to the pH within the fluid being tested, may be obtained.

The same fluid will then flow through the intermediate tube 29 and into the inlet 31 of the conductivity cell 9. Fluid will flow through the continuous bore 77 extending through the pH sensor assembly 5. The electrical conductors 91, 93 connected to each electrode of the conductivity sensor are coupled to an electronic device which converts the electronic signals therefrom into a value representing the physical property of conductivity. The general concept of measuring the conductivity of a fluid using a pair of electrodes is well known in the art. However, using the principles herein, the conductivity of the fluid flowing between the electrodes of the conductivity sensor may be continuously monitored and measured. After measurement of the conductivity, fluid will flow through the outlet tube and the either discarded or returned to its supply. Using the invention described herein, the pH and conductivity of various types of fluids used in various types of applications and in many different purposes may be monitored for pH and conductivity. The invention may be highly applicable in the biological science industry where the measurement of pH and conductivity for small volume of fluids is necessary. However, the invention is not limited to this type of application.

Although the invention has been described in connection with the embodiment depicted herein, various modifications and substitutions may be made to this embodiment without departing in any way from the scope of the invention as defined by the following claims.

What is claimed is:

1. A sensor for measuring at least one of pH and conductivity for fluids comprising:

a housing comprising a pH cell;

a pH cell fluid inlet disposed within said pH cell;

a pH cell fluid outlet disposed within said pH cell, said pH cell fluid inlet and said pH cell fluid outlet defining a pH fluid flow path therebetween;

an aperture within said pH cell adapted to receive an electronic pH probe therein, said aperture being configured to position an end of said electronic pH probe having a pH sensing area therein in juxtaposition to said pH fluid flow path, wherein fluid flowing within said fluid flow path is exposed to the pH sensing area of said electronic pH probe;

wherein said pH cell fluid inlet is located a distance upstream of said pH sensing area relative to a direction of intended flow; and wherein a portion of said flow path starting from said pH cell fluid inlet and ending at a point juxtaposed to said pH sensing area of said electronic pH probe progressively expands in width and decreases in depth.

2. The sensor of claim 1 wherein said housing comprises a conductivity cell, said conductivity cell being adapted for placement of a conductivity sensor therein, said conductivity sensor being disposed between a conductivity cell fluid inlet and a conductivity cell fluid outlet wherein fluid flowing from said conductivity cell fluid inlet through said conductivity cell fluid outlet contacts said conductivity sensor therebetween.

3. The sensor of claim 2 wherein said pH cell fluid outlet is adapted for placement in fluid flow relationship to said conductivity cell fluid inlet wherein fluid flowing from said pH cell fluid outlet will then flow into said conductivity cell fluid inlet.

4. The sensor of claim 3 further comprising means for retaining said electronic pH probe within said aperture of said pH cell.

5. The sensor of claim 4 wherein said retaining means comprises a threaded area adapted for receiving a retaining nut therein, said retaining nut having an aperture for retaining said electronic pH probe therethrough.

6. The sensor of claim 4 further comprising means for sealing fluid within said pH cell.

7. The sensor of claim 6 wherein said sealing means comprises an O-ring disposed on a lip of said pH probe, said O-ring contacting a ridge within said pH cell to form a fluid tight seal when said pH probe is inserted into said aperture.

8. The sensor of claim 6 wherein said pH fluid flow path is further defined by said end of said electronic pH probe having a pH sensing area inserted into a receptacle.

9. The sensor of claim 8 wherein a second portion of said flow path starting from a point juxtaposed to said pH sensing area of said electronic pH probe and ending at said pH cell fluid outlet progressively decreases in width.

10. The sensor of claim 9 wherein said pH cell fluid outlet is located a distance downstream of said pH sensing area relative to said direction of intended flow.

11. The sensor of claim 10 wherein the widest cross sectional area of said flow path adjacent said sensing area is between one and two times the cross sectional area of said pH cell fluid inlet.

12. The sensor of claim 11 wherein a portion of said end wall defining said flow path is oriented at an angle.

13. The sensor of claim 12 wherein said angle is approximately twelve degrees.

14. The sensor of claim 12 wherein a second portion of said end wall defining said flow path is oriented at a second angle.

15. The sensor of claim 14 wherein the second angle is the negative of the first angle.

16. The sensor of claim 2 or 14 wherein said conductivity sensor comprises a first positive electrode and a second negative electrode, said electrodes being separated by a gap therebetween.

17. The sensor of claim 16 wherein said conductivity sensor is further disposed to allow fluid flowing within said conductivity cell through said conductivity cell fluid inlet to flow into said gap between said electrodes.

18. The sensor of claim 17 wherein said electrodes each comprise an aperture extending therethrough, said aperture being disposed to allow said fluid flowing within said conductivity cell to flow therethrough and into said gap.

19. The sensor of claim 18 wherein said electrodes are disposed so that said apertures of each electrode are coaxially aligned.

20. The sensor of claim 19 wherein said apertures are coaxially aligned with said conductivity cell fluid inlet and said conductivity cell fluid outlet.

21. The sensor of claim 20 further comprising means for supporting said electrodes within said conductivity cell.

22. The sensor of claim 21 wherein said supporting means comprises a first receptacle in juxtaposition to a second receptacle, at least one of said first receptacle and said second receptacle being further oriented to maintain coaxial alignment between the apertures of said electrodes and to maintain said gap between said electrode.

23. The sensor of claim 22 wherein said electrodes are cylindrically shaped and wherein said apertures extend through the center of said cylindrically shaped electrodes.

24. The sensor of claim 23 further comprising means for sealing said conductivity sensor.

25. The sensor of claim 24 wherein said sealing means comprises a pair of O-rings, each of said pair of O-rings being disposed about said electrodes to prevent fluid from flowing outside of said apertures.

26. The sensor of claim 25 wherein each electrode comprises a means for connecting an electrical conductor thereto.

27. The sensor of claim 26 wherein said O-rings contact a top surface of said conductivity cell and bottom surface of said conductivity cell, respectively.

28. The sensor of claim 27 further comprising a cap adapted to cover an opening to said conductivity cell.

29. The sensor of claim 28 wherein at least a portion of said conductivity cell is filled with a potting material.

30. The sensor of claim 29 further comprising means for securing said sensor.

31. The sensor of claim 30 further comprising a compression fitting in fluid flow relationship to said pH cell fluid inlet.

32. The sensor of claim 31 further comprising a compression fitting in fluid flow relationship to said conductivity cell fluid outlet.

33. A method of measuring at least one of pH and conductivity comprising:

flowing a fluid in a stream into a pH cell fluid inlet, said pH cell fluid inlet located a distance upstream of a pH sensing area of an electronic pH probe relative to a direction of intended flow;

passing said fluid past said electronic pH probe thereby electronically measuring the pH of said fluid;

widening the stream of fluid from said pH cell fluid inlet and as it passes said pH sensing area of said electronic pH probe so that said stream covers said sensing area;

making the stream of fluid more shallow as it passes the pH sensing area; and sensing the pH of said fluid within said stream covering said sensing area.

34. The method of claim 33 wherein the widest cross sectional area of the fluid passing before said sensing area is between one and two times the cross sectional area of the fluid passing into the pH cell fluid inlet.

35. The method of claim 33 or 34 further comprising flowing said fluid into a conductivity cell wherein the conductivity of said fluid is measured.

36. The method of claim 35 wherein said fluid is flowed in a stream into a gap located between electrodes of a conductivity sensor in said conductivity cell.

37. The method of claim 36 wherein said fluid is flowed into an aperture extending through said electrodes.

38. A sensor for measuring pH and conductivity for fluids comprising:

a housing comprising a pH cell and a conductivity cell;

a pH cell fluid inlet disposed within said pH cell;

a pH cell fluid outlet disposed within said pH cell, said pH cell fluid inlet and said pH cell fluid outlet defining a pH fluid flow path therebetween; and an aperture within said pH cell adapted to receive an electronic pH probe therein, said aperture being configured to position an end of said electronic pH probe having a pH sensing area therein in juxtaposition to said pH fluid flow path, wherein fluid flowing within said fluid flow path is exposed to the pH sensing area of said electronic pH probe;

wherein a portion of said flow path starting from said pH cell fluid inlet and ending at a point juxtaposed to said pH sensing area of said electronic PH probe progressively expands in width.

39. The sensor of claim 38 wherein said conductivity cell being adapted for placement of a conductivity sensor therein, said conductivity sensor being disposed between a conductivity cell fluid inlet and a conductivity cell fluid outlet wherein fluid flowing from said conductivity cell fluid inlet through said conductivity cell fluid outlet contacts said conductivity sensor therebetween.

40. The sensor of claim 39 wherein said pH cell fluid outlet is in fluid flow relationship to said conductivity cell fluid inlet wherein fluid flowing from said pH cell fluid outlet will then flow into said conductivity cell fluid inlet.

41. The sensor of claim 40 wherein said housing comprises a threaded area adapted for receiving a retaining nut therein, said retaining nut having an aperture for retaining said electronic pH probe therethrough.

42. The sensor of claim 41 further comprising an O-ring disposed on a lip of said pH probe, said O-ring contacting a ridge within said pH cell to form a fluid tight seal when said pH probe is inserted into said aperture.

43. The sensor of claim 42 wherein said pH fluid flow path is further defined by said end of said electronic pH probe having a pH sensing area inserted into said receptacle.

44. The sensor of claim 43 wherein said pH cell fluid inlet is located a distance upstream of said pH sensing area relative to a direction of intended flow.

45. The sensor of claim 44 wherein a second portion of said flow path starting from a point juxtaposed to said pH sensing area of said electronic pH probe and ending at said pH cell fluid outlet progressively decreases in width.

46. The sensor of claim 45 wherein the widest cross sectional area of said flow path adjacent said sensing area is between one and two times the area of said pH cell fluid inlet.

47. The sensor of claim 46 wherein a portion of said end wall defining said flow path is oriented at an angle.

48. The sensor of claim 47 wherein said angle is approximately twelve degrees.

49. The sensor of claim 48 wherein a second portion of said end wall defining said flow path is oriented at a second angle.

50. The sensor of claim 49 wherein the second angle is the negative of the first angle.

51. The sensor of claim 50 wherein said conductivity sensor comprises a positive electrode and a negative electrode, said electrodes being separated by a gap therebetween.

52. A conductivity sensor comprising:

a positive electrode;

a negative electrode, said negative and positive electrodes being separated by a gap;

said sensor being adapted for placement between a fluid inlet and outlet of a conductivity cell wherein fluid entering said inlet flows into said gap;

wherein said electrodes each have an aperture extending therethrough, said aperture being disposed to allow said fluid flowing within said conductivity cell to flow therethrough and into said gap;

wherein sad electrodes are disposed so that said apertures of each electrode are coaxially aligned;

wherein said apertures are coaxially aligned with said conductivity cell fluid inlet and said conductivity cell fluid outlet; and means for supporting said electrodes within said conductivity cell;

wherein said supporting means comprises a first receptacle in juxtaposition to a second receptacle, said receptacles being oriented to maintain coaxial alignment between the apertures of said electrodes and to maintain said gap between said electrodes.

53. The conductivity sensor of claim 52 wherein said apertures extend through the center of said electrodes, said electrodes being cylindrically shaped.

54. The conductivity sensor of claim 53 further comprising means for sealing said conductivity sensor.

55. The conductivity sensor of claim 54 wherein said sealing means comprises a pair of O-rings, each of said pair of O-rings being disposed about said electrodes to prevent fluid from flowing outside of said apertures.

56. The conductivity sensor of claim 56 wherein each electrode comprises a means for connecting an electrical conductor thereto.

57. The conductivity sensor of claim 56 wherein said O-rings contact a top surface of said conductivity cell and bottom surface of said conductivity cell, respectively.

58. The conductivity sensor of claim 57 further comprising a cap adapted to cover an opening to said conductivity cell.

59. The conductivity sensor of claim 58 wherein at least a portion of said conductivity cell is filled with a potting material.

* * * * *